(12) United States Patent
Kim et al.

(10) Patent No.: US 7,205,395 B2
(45) Date of Patent: Apr. 17, 2007

(54) PROCESS OF PREPARING AZITHROMYCIN AND CRYSTALLINE 9-DEOXO-9A-AZA-9A-HOMOERYTHROMYCIN A HYDRATE USED THEREIN

(75) Inventors: Gi Jeong Kim, Seoul (KR); Mi Ra Seong, Seongnam-si (KR); Sang Min Yun, Seongnam-si (KR); Kwee Hyun Suh, Icheon-si (KR)

(73) Assignee: Hanmi Pharm Co., Ltd., Kyungki-do (KR)

( * ) Notice: Subject to any disclaimer, the term of this patent is extended or adjusted under 35 U.S.C. 154(b) by 237 days.

(21) Appl. No.: 10/509,934

(22) PCT Filed: Apr. 3, 2002

(86) PCT No.: PCT/KR02/00588

§ 371 (c)(1),
(2), (4) Date: Oct. 1, 2004

(87) PCT Pub. No.: WO03/082889

PCT Pub. Date: Oct. 9, 2003

(65) Prior Publication Data
US 2005/0119468 A1    Jun. 2, 2005

(51) Int. Cl.
*C07H 17/08* (2006.01)
(52) U.S. Cl. ..................... 536/7.4; 536/18.5
(58) Field of Classification Search ............. 536/7.4, 536/18.5
See application file for complete search history.

(56) References Cited

U.S. PATENT DOCUMENTS 4,328,334 A    5/1982   Kobrehel et al.

FOREIGN PATENT DOCUMENTS

| EP | 0 298 650 A2 | 1/1989 |
|---|---|---|
| EP | 0 307 128 A2 | 3/1989 |
| EP | 0 879 823 A1 | 11/1998 |
| EP | 0 941 999 A2 | 9/1999 |
| EP | 0 984 020 A2 | 3/2000 |

*Primary Examiner*—Elli Peselev
(74) *Attorney, Agent, or Firm*—Sughrue Mion, PLLC

(57) ABSTRACT

Azithromycin is prepared in a high yield by a simple process using a crystalline 9-deoxo-9a-aza-9a-homoerythromycin A hydrate.

9 Claims, 2 Drawing Sheets

PROCESS OF PREPARING AZITHROMYCIN AND CRYSTALLINE 9-DEOXO-9A-AZA-9A-HOMOERYTHROMYCIN A HYDRATE USED THEREIN

The present disclosure relates to subject matter contained in and claims benefit of priority from PCT/KR02/00588, filed Apr. 3, 2002. The entire disclosure of the prior application is hereby incorporated by reference.

FIELD OF THE INVENTION

The present invention relates to a method of preparing azithromycin using a crystalline 9-deoxo-9a-aza-9a-homoerythromycin A hydrate as an intermediate, and a novel precursor thereof, crystalline 9-deoxo-9a-aza-9a-homoerythromycin A hydrate, and a process for the preparation thereof.

BACKGROUND OF THE INVENTION

Azithromycin, 9-deoxo-9a-aza-9a-methyl-9a-homoerythromycin A (IUPAC name: N-methyl-11-aza-10-deoxo-10-dihydroerythromycin A), is an azalide-based semisynthetic macrolide antibiotic of formula (I) which is very effective in treating respiratory organ diseases, sexual contact infection, skin infection diseases and the like, as disclosed in U.S. Pat. Nos. 4,517,359 and 4,474,768 (Kirst and Sides, *Antimicrob. Agents Chemother.*, 33, 1419(1989)):

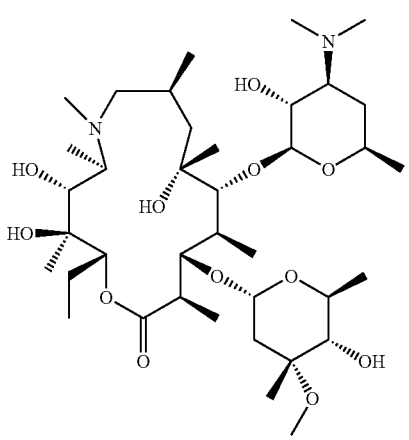
(I)

Generally, azithromycin is prepared by conducting conventional Eschweiler-Clarke reductive N-methylation (Eschweiler and Clarke, *Org. React.*, 5, 290(1945)) of the 9a-positon of 9-deoxo-9a-aza-9a-homoerythromycin A of formula (II), as described in U.S. Pat. No. 4,517,359, or by protecting the 3'-nitrogen of 9-deoxo-9a-aza-9a-homoerythromycin A of formula (II) with N-oxide, conducting N-methylation of the 9a-position thereof and then removing the N-oxide protecting group, as described in U.S. Pat. No. 4,474,768. The compound of formula (II) is thus a very important precursor in the preparation of azithromycin.

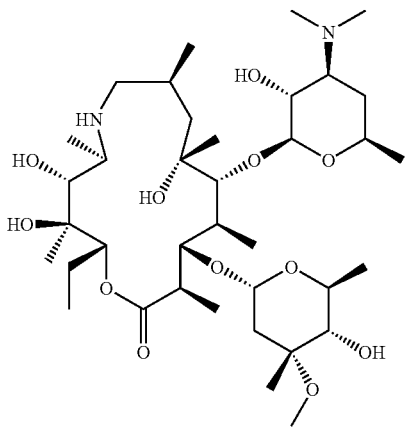
(II)

9-Deoxo-9a-aza-9a-homoerythromycin A of formula (II) may be prepared by reducing 9-deoxo-6-deoxy-6,9-epoxy-9,9a-didehydro-9a-aza-homoerythromycin A (simply, 6,9-imino ether) of formula (III) which is prepared from erythromycin A 9-oxime in accordance with a conventional method (Djokic et al., *J. Chem. Soc. Perkin Trans. I*, 1881(1986)).

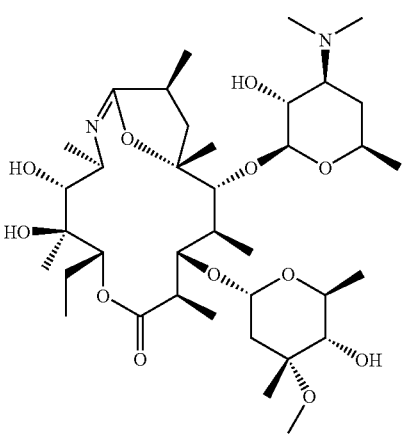
(III)

For example, U.S. Pat. Nos. 4,328,334 and 6,013,778 disclose a method of preparing the compound of formula (II) from the compound of formula (III) by way of conducting hydrogenation under a high hydrogen pressure in the presence of a rhodium(Rh), platinum(Pt), palladium(Pd) or ruthenium(Ru) metal or metal oxide catalyst; and Austrian Patent No. 8,600,536, by way of conducting electrical reduction. However, these methods have the problem that they require the use of an expensive precious metal catalyst and a high hydrogen pressure of 65 psi or higher, or that electrical reduction is not suitable for mass-production.

U.S. Pat. No. 4,328,334 discloses a method of preparing the compound of formula (II) by reducing the compound of formula (III) in a methanol solution maintained at 4° C. with a reducing agent such as $NaBH_4$. However, this method requires a large excess amount of $NaBH_4$ (16 mole equivalents or more) and the reduction product existing in the form of a borate complex must be subjected to further hydrolysis using an inorganic acid such as hydrochloric acid, the hydrolysis reaction inducing a side reaction to produce a large -quantity of impurities (Djokic et al., *J. Chem. Soc. Perkin Trans. I,* 1881(1986)).

International Publication Patent No. WO 94/26758 teaches that 9-deoxo-9a-aza-9a-homoerythromycin A of formula (II) may be prepared by hydrogenating erythromycin A 9-oxime or 9-deoxo-11-deoxy-9,11-epoxy-9,9a-didehydro-9a-aza-homoerythromycin (simply, 9,11-imino ether) of formula (IV) prepared from 6,9-imino ether of formula (III) under a high pressure in the presence of $PtO_2$. However, this method suffers from a high manufacturing cost.

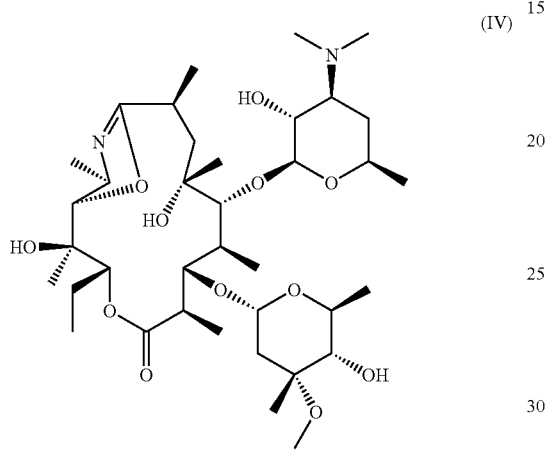

(IV)

Therefore, there exists a demand for a simple method which is capable of providing 9-deoxo-9a-aza-9a-homoerythromycin A of formula (II) in a simple, economic way.

Accordingly, the present inventors have endeavored to develop such a method and have found that pure crystalline hydrate of 9-deoxo-9a-aza-9a-homoerythromycin A of formula (II) can be prepared in a high yield by reducing 6,9-imino ether of formula (III) with a small amount of $NaBH_4$ at −20 to −10° C. and treating the reaction mixture with an acidic solution of citric acid, followed by neutralization.

SUMMARY OF THE INVENTION

Accordingly, it is a primary object of the present invention to provide a simple, high-yield process for preparing azithromycin.

It is another object of the present invention to provide a crystalline 9-deoxo-9a-aza-9a-homoerythromycin A hydrate used as a precursor in the preparation of azithromycin, and a process for the preparation thereof.

In accordance with one aspect of the present invention, there is provided a method of preparing azithromycin of formula (I) comprising the steps of: (a) reducing 6,9-imino ether of formula (III) dissolved in methanol with 5 to 7 mole equivalents of $NaBH_4$ at −20 to −10° C., treating the reaction mixture with an acidic aqueous acetone solution of citric acid, and adjusting the solution pH to 10.5 to 12.0 to obtain a crystalline hydrate of 9-deoxo-9a-aza-9a-homoerythromycin A of formula (II); and (b) N-methylating the compound of formula (II) prepared in step (a) with an aqueous formaldehyde-formic acid mixture in an organic solvent:

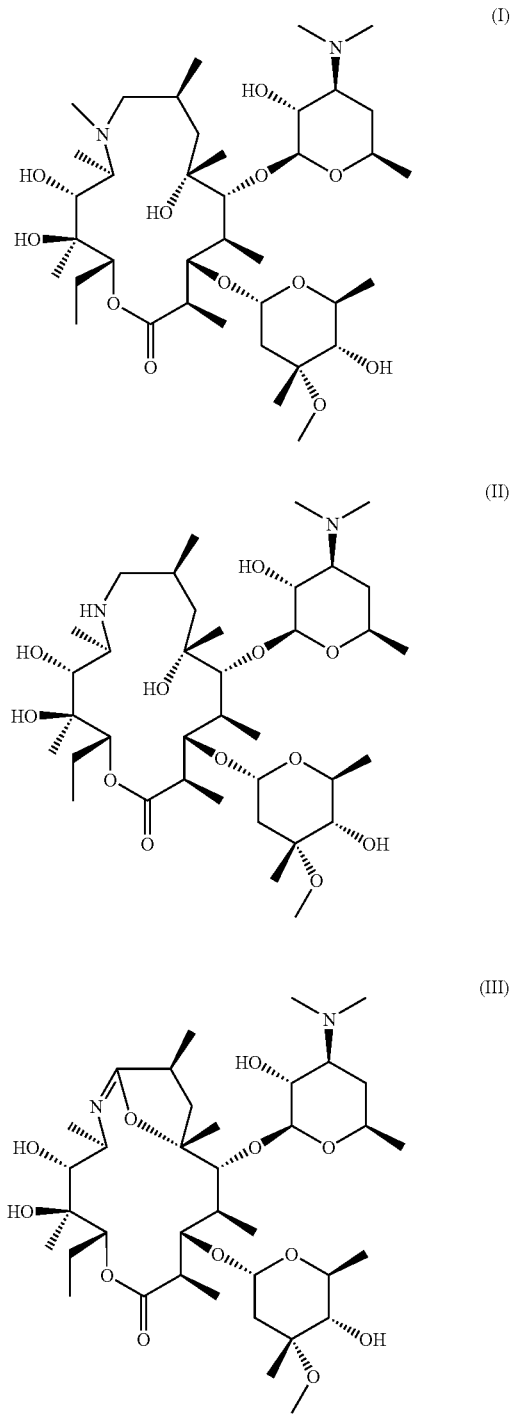

In accordance with another aspect of the present invention, there is provided a crystalline hydrate of 9-deoxo-9a-aza-9a-homoerythromycin A of formula (II) used as a precursor in the preparation of azithromycin; and a method of preparing same comprising the steps of: (i) reducing 6,9-imino ether of formula (III) dissolved in methanol with 5 to 7 mole equivalents of $NaBH_4$ at −20 to −10° C., (ii) treating the reaction mixture with an acidic aqueous acetone solution of citric acid, and (iii) adjusting the solution pH to 10.5 to 12.0.

BRIEF DESCRIPTION OF THE DRAWINGS

The above and other objects and features of the present invention will become apparent from the following description of the invention taken in conjunction with the following accompanying drawings, which respectively show.

DETAILED DESCRIPTION OF THE INVENTION

Figure 1:
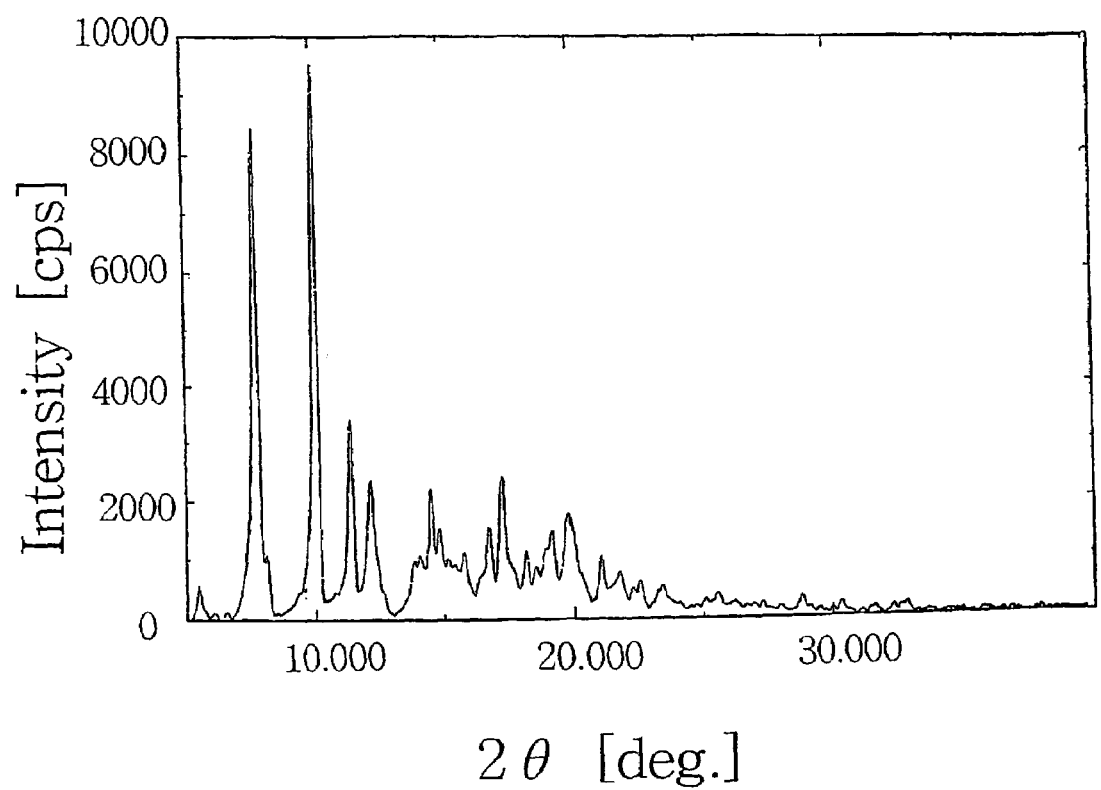
FIG. 1: a powder X-ray diffraction scan of the crystalline 9-deoxo-9a-aza-9a-homoerythromycin A hydrate prepared in accordance with the inventive method.
Figure 2:
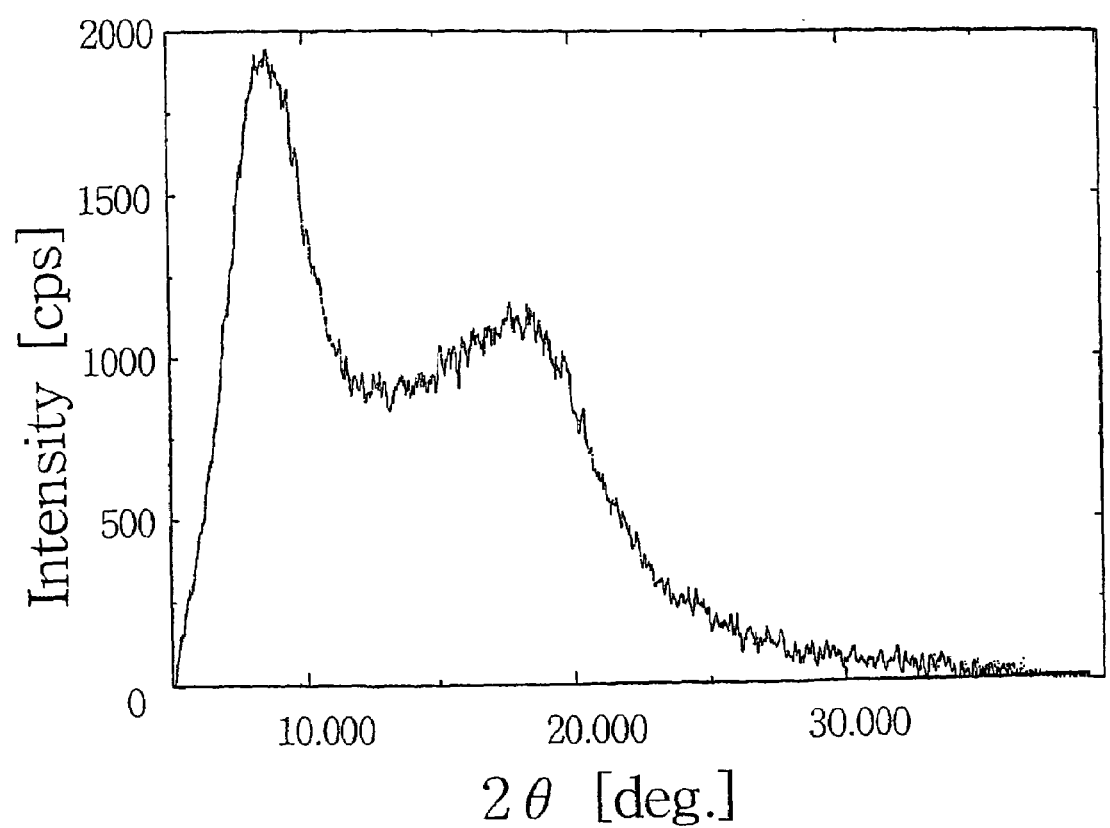
FIG. 2: a powder X-ray diffraction scan of 9-deoxo-9a-aza-9a-homoerythromycin A prepared in accordance with a conventional method.

The method of the present invention is described in detail as follows:

Step (a)

A methanol solution of the 6,9-imino ether of formula (III) prepared, e.g., by a conventional method (Djokic et al., J. Chem. Soc. Perkin Trans. I, 1881(1986)) is chilled to −20 to −10° C., $NABH_4$ is added thereto in an amount ranging from 5 to 7 mole equivalents based on the amount of the 6,9-imino ether, and then stirred at the same temperature for a period ranging from 4 to 6 hrs. After completion of the reduction reaction, the reaction solution is concentrated, water and an organic solvent such as dichloromethane, chloroform and 1,2-dichloroethane are added to the resulting residue, and then the organic layer is separated and concentrated.

To the resulting residue, water and acetone are added, followed by adding citric acid in an amount ranging from 1 to 20 mole equivalents based on the amount of the 6,9-imino ether. The pH of the mixture is adjusted to 2.0 to 3.0 with HCl at a temperature of 0° C. to room temperature, and stirred for at least 30 min. As can be confirmed by thin layer chromatography, citric acid hydrolyzes the borate complex of the reduction product efficiently without inducing undesirable side reaction. Then, the solution pH is adjusted to 10.5 to 12.0 at a temperature of 0° C. to room temperature to induce precipitation of crystals. The precipitated crystals are filtered and dried at 40° C. to give a pure monohydrate form of crystalline hydrate of 9-deoxo-9a-aza-9a-homoerythromycin A of formula (II) having a melting point of 126 to 130° C. and a moisture content of 2.0 to 3.5% (determined by Kaal-Fisher moisture measurement) in a high yield of 85% or higher. The amount of acetone used is preferably in the range of 1 to 5 ml per 1 g of the compound of formula (III), and water, in a volume ranging from 1 to 4 folds of the acetone volume.

If necessary, the crystalline hydrate of formula (II) thus obtained may be further recrystallized from a mixed solvent of water and an organic solvent such as acetone, methanol and acetonitrile to improve the purity thereof Preferably, the pH of the recrystallized solution is adjusted to 10.5 or higher, and the amount of the organic solvent used is in the range of 1 to 2 ml per 1 g of the crystalline hydrate, the water to organic solvent volume ratio being in the range of 1 to 4.

The crystalline hydrate of 9-deoxo-9a-aza-9a-homoerythromycin A of formula (II) obtained in accordance with the present invention is completely free of boron-containing impurities and it is a novel compound which is characteristically different from the well-known, amorphous anhydrous 9-deoxo-9a-aza-9a-homoerythromycin A prepared by prior methods (U.S. Pat. Nos. 4,328,334 and 6,013,778, and International Publication Patent No. 94/26758) as judged by its melting point, moisture content and powder X-ray diffraction pattern, as shown in Table.

TABLE

| Physical properties | Inventive powder | Conventional powder |
|---|---|---|
| Shape | Crystalline powder | Amorphous powder |
| Melting point | 126–130° C. | 113–116° C. |
| Moisture content | 2.0–3.5% | Below 1% |
| 2 theta value of powder X-ray diffraction peaks ($I/I° \geq 10$) | 7.700° ± 0.2, 8.080° ± 0.2, 10.080° ± 0.2, 11.440° ± 0.2, 12.200° ± 0.2, 13.840° ± 0.2, 14.100° ± 0.2, 14.520° ± 0.2, 14.820° ± 0.2, 15.140° ± 0.2, 15.800° ± 0.2, 16.780° ± 0.2, 17.260° ± 0.2, 18.160° ± 0.2, 18.900° ± 0.2, 19.180° ± 0.2, 19.800° ± 0.2, 21.040° ± 0.2 | No observable diffraction peaks |

Step (b)

In accordance with the present invention, the crystalline hydrate of 9-deoxo-9a-aza-9a-homoerythromycin A of formula (II) obtained in step (a) is subjected to conventional Eschweiler-Clarke reductive N-methylation (Eschweiler and Clarke, Org. React., 5, 290(1945)), i.e., reacted with a formic acid-aqueous formaldehyde mixture in an organic solvent which may be a halogenized solvent such as dichloromethane, chloroform, carbon tetrachloride and 1,2-dichloroethane; an alcohol such as methanol, ethanol and isopropanol; a ketone such as acetone, ethylmethylketone and isobutylmethylketone; and an ester such as methyl acetate, ethyl acetate and isopropyl acetate, to give azithromycin of formula (I) in a high yield of at least 90%. The amounts of formic acid and formaldehyde used are each independently in the range of 1 to 3 mole equivalents based on the amount of the crystalline hydrate of 9-deoxo-9a-aza-9a-homoerythromycin A of formula (II), and the reaction may be performed at a temperature ranging from room temperature to the boiling point of the solvent.

The following Examples are given for the purpose of illustration only, and are not intended to limit the scope of the invention.

EXAMPLE 1

Preparation of crystalline 9-deoxo-9a-aza-9a-homoerythromycin A hydrate 27.31 g (37.4 mmol) of 9-deoxo-6-deoxy-6,9-epoxy-9,9a-didehydro-9a-aza-homoerythromycin A (6,9-imino ether) prepared by a conventional method (Djokic et al., J. Chem. Soc. Perkin Trans. I, 1881(1986)) was dissolved in 150 ml of methanol and then cooled to −15° C. 8.40 g (222.1 mmol) of $NaBH_4$ is added thereto in small portions and stirred at −15° C. for 4 hrs. The mixture was then slowly heated to room temperature and concentrated under reduced pressure. Then, chloroform and water were added to the resulting residue, the organic layer was separated and concentrated. 100 ml of water and 60 ml of acetone were poured to the resulting residue, and 23.1 g (109.9 mmol) of citric acid monohydrate was added thereto. After citric acid was dissolved, pH of the solution was adjusted to 2.5 with 6N-hydrochloric acid and stirred at room temperature for 30 min. The resulting solution was cooled to below 10° C., 20% sodium hydroxide was slowly added thereto to adjust the pH to 11.5, and stirred at the same temperature for 1 hr. The precipitated crystals were filtered, washed with cold water and dried at 40° C. overnight to obtain 23.5 g of the title compound (yield: 85.5%).

m.p.: 126–130° C.

moisture content: 2.5%

2θ values of powder X-ray diffraction peaks (I/I°≧10): 7.700°±0.2, 8.080°±0.2, 10.080°±0.2, 11.440°±0.2, 12.200°±0.2, 13.840°±0.2, 14.100°±0.2, 14.520°±0.2, 14.820°±0.2, 15.140°±0.2, 15.800°±0.2, 16.780°±0.2, 17.260°±0.2, 18.160°±0.2, 18.900°±0.2, 19.180°±0.2, 19.800°±0.2, 21.040°±0.2

EXAMPLE 2

Purification of crystalline 9-deoxo-9a-aza-9a-homoerythromycin A hydrate 20 g of the crystalline 9-deoxo-9a-aza-9a-homoerythromycin A hydrate obtained in Example was dissolved in 30 ml of acetone, and 90 ml of water was added thereto at room temperature. The solution pH was adjusted to above 10.5 with a dilute sodium hydroxide solution, cooled to below 10° C. and stirred for 1 hr. The precipitated crystals was filtered, washed with cold water and dried at 40° C. overnight to obtain 18.8 g of a purified form of the title compound (recovery: 94%).

EXAMPLE 3

Purification of crystalline 9-deoxo-9a-aza-9a-homoerythromycin A hydrate

The procedure of Example 2 was repeated except that methanol was used instead of acetone, to obtain a purified form of the title compound (recovery: 90%).

EXAMPLE 4

Purification of crystalline 9-deoxo-9a-aza-9a-homoerythromycin A hydrate

The procedure of Example 2 was repeated except that acetonitrile was used instead of acetone, to obtain a purified form of the title compound (recovery: 920/%).

EXAMPLE 5

Preparation of azithromycin 22.05 g (30.0 mmol) of the crystalline 9-deoxo-9a-aza-9a-homoerythromycin A hydrate obtained in Examples 1 to 4 was dissolved in 100 ml of chloroform, 2.3 ml of formic acid and 4.7 ml of a 35% aqueous formaldehyde solution were added thereto, and refluxed for 7 hrs. The reaction solution was cooled to room temperature, 100 ml of water was added thereto, and the pH was adjusted to 2.5 with 6N-hydrochloric acid. The organic layer was removed. 150 ml of chloroform was added to the aqueous layer, the pH was adjusted to 11.0 with a dilute sodium hydroxide solution, and the organic layer was separated. The organic layers were combined, concentrated under a reduced pressure, and the resulting residue was recrystallized from an ethanol-water mixture. The resulting crystals were filtered, washed with water and dried at 45° C. to obtain 20.2 g of the title compound (yield: 90%).

As shown above, the method of the present invention is simple and gives azithromycin in a high yield.

While the invention has been described with respect to the above specific embodiments, it should be recognized that various modifications and changes may be made to the invention by those skilled in the art which also fall within the scope of the invention as defined by the appended claims.

What is claimed is:

1. A method of preparing azithromycin of formula (I) comprising the steps of: (a) reducing 6,9-imino ether of formula (III) dissolved in methanol with 5 to 7 mole equivalents of NaBH$_4$ at −20 to −10° C., treating the reaction mixture with an acidic aqueous acetone solution of citric acid, and adjusting the solution pH to 10.5 to 12.0 to obtain a crystalline hydrate of 9-deoxo-9a-aza-9a-homoerythromycin A of formula (II); and (b) N-methylating the compound of formula (II) prepared in step (a) with an aqueous formaldehyde-formic acid mixture in an organic solvent:

(I)

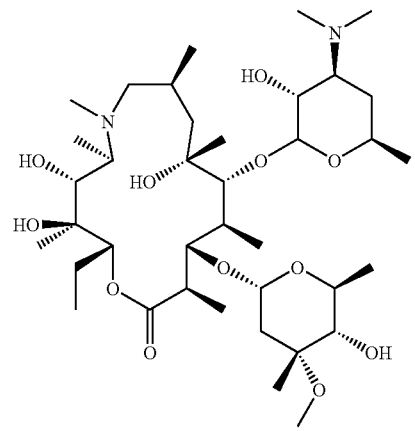

2. The method of claim 1, wherein citric acid is used in an amount ranging from 1 to 20 mole equivalents based on 1 mole of 6,9-imino ether of formula (III).

3. The method of claim 1, wherein the pH of the acidic solution is in the range of 2.0 to 3.0.

4. The method of claim 1, wherein the amount of acetone in the aqueous acetone solution is in the range of 1 to 5 ml per 1 g of the compound of formula (III), and the water to acetone volume ratio is in the range of 1 to 4.

5. The method of claim 1, wherein the organic solvent used in step (b) is selected from the group consisting of dichloromethane, chloroform, carbon tetrachloride, 1,2-dichloroethane, methanol, ethanol, isopropanol, acetone, ethylmethylketone, isobutylmethyl-ketone, methyl acetate, ethyl acetate, isopropyl acetate and a mixture thereof.

6. The method of claim 1, wherein the amounts of formic acid and formaldehyde used are each independently in the range of 1 to 3 mole equivalents per 1 mole of the compound of formula (II).

7. A method of preparing a crystalline hydrate of 9-deoxo-9a-aza-9a-homoerythromycin A of formula (II) comprising the steps of: (i) reducing 6,9-imino ether of formula (III) dissolved in methanol with 5 to 7 mole equivalents of NaBH$_4$ at −20 to −10° C., (ii) treating the reaction mixture with an acidic aqueous acetone solution of citric acid, and (iii) adjusting the solution pH to 10.5 to 12.0:

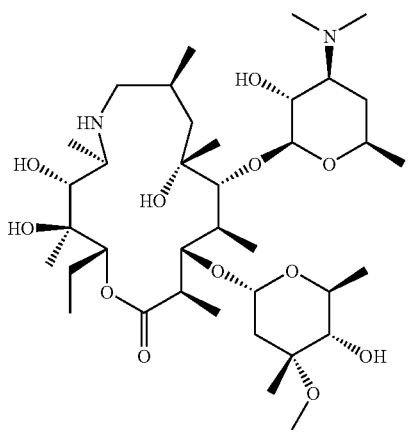

(II)

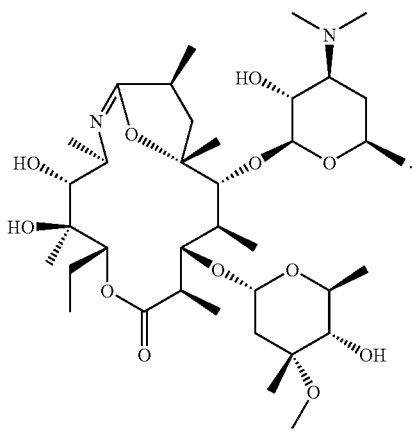

(III)

8. The method of claim 7 which further comprises the step of recrystallizing the crystalline hydrate from a mixture of water and an organic solvent selected from acetone, methanol and acetonitrile.

9. The method of claim 8, wherein the organic solvent is used in an amount ranging from 1 to 2 ml per 1 g of the crystalline hydrate, and the water to organic solvent volume ratio is in the range of 1 to 4.

* * * * *